United States Patent [19]

Wingen et al.

[11] Patent Number: 5,702,638
[45] Date of Patent: Dec. 30, 1997

[54] PHENANTHRIDINE DERIVATIVES, AND THEIR USE IN LIQUID-CRYSTALLINE MIXTURES

[75] Inventors: Rainer Wingen, Hattersheim; Barbara Hornung, Hasselroth, both of Germany

[73] Assignee: Hoechst Aktiengesellschaft, Frankfurt, Germany

[21] Appl. No.: 676,301

[22] PCT Filed: Jan. 30, 1995

[86] PCT No.: PCT/EP95/00312

§ 371 Date: Jul. 17, 1996

§ 102(e) Date: Jul. 17, 1996

[87] PCT Pub. No.: WO95/21227

PCT Pub. Date: Aug. 10, 1995

[51] Int. Cl.$^6$ .................. C09K 19/32; C07D 221/12; G02F 1/13
[52] U.S. Cl. .................. 252/299.62; 546/108; 349/182
[58] Field of Search .................. 252/299.01, 299.62; 546/108; 349/182

[56] References Cited

FOREIGN PATENT DOCUMENTS

| | | |
|---|---|---|
| 56/118070 | 9/1981 | Japan . |
| 43/64128 | 12/1992 | Japan . |
| 51/048239 | 6/1993 | Japan . |

OTHER PUBLICATIONS

CA:75:98029, 1971.

*Primary Examiner*—Shean C. Wu
*Attorney, Agent, or Firm*—Curtis, Morris & Safford, P. C.

[57] ABSTRACT

Phenanthridine derivatives, and their use in liquid-crystalline mixtures

A ferroelectric liquid-crystal mixture containing one or more phenanthridine derivatives of the formula (I)

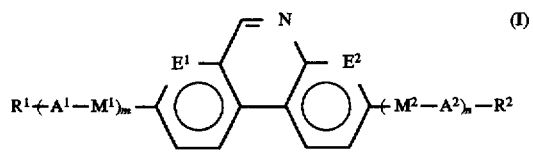

$E^1$ and $E^2$ are identical or different and are —N—, —CF— or —CH—;
$R^1$ and $R^2$ are identical or different and are, for example, a straight-chain or branched alkyl radical having 1 to 20 carbon atoms;
Q is —CH$_2$—O—, —CO—O— or a single bond;
$M^1$ and $M^2$ are identical or different and are —CO—O—, —O—CO—, —CH$_2$—O—, —O—CH$_2$—, —CH$_2$—CH$_2$—, —C≡C—, or a single bond;
$A^1$ and $A^2$ are identical or different and are 1,4-phenylene, in which one or more H atoms may be replaced by F, trans-1,4-cyclohexylene, pyrimidine-2,5-diyl, pyridine-2,5-diyl, where one H atom may be replaced by F, 1,3,4-thiadiazole-2,5-diyl, 1,3-dioxane-2,5-diyl, 1,3-dithiane-2,5-diyl, 1,3-thiazole-2,4-diyl, 1,3-thiazole-2,5-diyl, thiophene-2,4-diyl or thiophene-2,5-diyl;

m and n are zero or one, but their sum is at most one.

Even addition of only small amounts of phenanthridine derivatives of the formula (I) gives ferroelectric liquid-crystal mixtures having high negative values for the dielectric anisotropy.

6 Claims, No Drawings

PHENANTHRIDINE DERIVATIVES, AND THEIR USE IN LIQUID-CRYSTALLINE MIXTURES

This application is a 371 of PCT/EP95/00312 filed Jan. 30, 1995.

BACKGROUND OF THE INVENTION

1. Field of the Invention

In addition to nematic and cholesteric liquid crystals, optically active tilted smectic (ferroelectric) liquid crystals have also been used recently in commercial display devices.

Clark and Lagerwall have been able to show that the use of ferroelectric liquid crystals (FLCs) in very thin cells results in optoelectrical switching or display elements which have response times faster by a factor of up to 1000 compared with conventional TN ("twisted nematic") cells (see, for example, EP-A 0 032 362). On the basis of this and other favorable properties, for example the possibility of bistable switching and the virtually viewing angle-independent contrast, FLCs are fundamentally highly suitable for areas of application such as computer displays.

For the use of FLCs in electro-optical or fully optical components, either compounds are required which form tilted or orthogonal smectic phases and are themselves optically active, or ferroelectric smectic phases can be induced by doping compounds which, although forming such smectic phases, are not themselves optically active, with optically active compounds. The desired phase should be stable over the broadest possible temperature range.

In order to achieve good contrast in electro-optical components, a uniform planar alignment of the liquid crystals is necessary. Good alignment in the $S_A$ and $S*_C$ phase can be achieved, for example, if the phase sequence of the liquid-crystal mixture is, with decreasing temperature:

$$\text{isotropic} \rightarrow N^* \rightarrow S_A \rightarrow S*_C$$

The prerequisite is that the pitch of the helix in the N* phase is very large (greater than 10 μm) or, even better, is fully compensated (see, for example, T. Matsumoto et al., pp. 468-470, Proc. of the 6th Int. Display Research Conf., Japan Display, Sept. 30-Oct. 2, 1986, Tokyo, Japan; M. Murakami et al., ibid. pp. 344-347). This is achieved by adding one or more optically active dopes which induce a right-hand helix to the chiral liquid-crystal mixture which has, for example, a left-hand helix in the N* phase, in such amounts that the helix is compensated.

A further prerequisite for the use of the SSFLCD effect (surface-stabilized ferroelectric liquid-crystal display) of Clark and Lagerwall for uniform planar alignment is that the pitch in the smectic C* phase is significantly greater than the thickness of the display element (Mol. Cryst. Liq. Cryst. 94 (1983), 213-134 and 114 (1984), 151-187). As in the case of the cholesteric pitch, this is achieved by using dopes having the opposite rotation of the helix.

The optical response time τ [μs] of ferroelectric liquid-crystal systems, which should be as short as possible, depends on the rotational viscosity of the system γ[mPas], the spontaneous polarization $P_s$[nC/cm$^2$] and the electric field strength E[V/m], in accordance with the equation

$$\tau \sim \frac{\gamma}{P_s \cdot E}$$

Since the field strength E is determined by the electrode separation in the electro-optical component and by the applied voltage, the ferroelectric display medium must have low viscosity and a high spontaneous polarization to achieve a short response time.

Finally, in addition to thermal, chemical and photochemical stability, a small optical anisotropy Δn, preferably≈0.13, and a low positive or preferably negative dielectric anisotropy Δε are required (see, for example, S. T. Lagerwall et al., "Ferroelectric Liquid Crystals for Displays", SID Symposium, Oct. Meeting 1985, San Diego, Calif., USA).

The totality of these requirements can only be achieved by means of mixtures comprising a plurality of components. The base (or matrix) used preferably comprises compounds which if possible themselves already have the desired phase sequence $I \rightarrow N \rightarrow S_A \rightarrow S_C$. Further components of the mixture are frequently added in order to reduce the melting point and to broaden the $S_C$ and usually also the N phase, to induce optical activity, for pitch compensation and to match the optical and dielectric anisotropy, although the rotational viscosity, for example, should if possible not be increased.

Ferroelectric liquid-crystal displays can also be operated by utilizing the DHF (distorted helix formation) effect or the PSFLCD effect (pitch-stabilized ferroelectric liquid-crystal display, also known as SBF=short pitch bistable ferroelectric effect). The DHF effect has been described by B. I. Ostrovski in Advances in Liquid Crystal Research and Applications, Oxford/Budapest, 1980, 469 ff.; the PSFLCD effect is described in DE-A 39 20 625 and EP-A 0 405 346. In contrast to the SSFLCD effect, utilization of these effects requires a liquid-crystalline material having a short $S_C$ pitch.

Derivatives of phenanthrene (which also include 9,10-dihydrophenanthrenes here) have already been described as liquid crystals or as components of liquid-crystalline mixtures:

azomethines containing a phenanthrene or 9,10-dihydrophenanthrene unit (J. Chem. Soc. [London](1958) 552; J. Chem. Soc., Perkin II (1982) 465); keto derivatives of 9,10-dihydrophenanthrene or of phenanthrene (Chem. Ind. [London] (1974) 615; Prod. Int. Liq. Cryst. Conf. (1973) 397; Tetrahedron 37, 2815 (1981)); carboxyl derivatives of 9,10-dihydrophenanthrene (German Democratic Republic Patent 153 826); 2,7-bis(alkoxy)phenanthrenes (Nippon Kagaku Kaishi (1980) 250) and 9,10-dihydrophenanthrenes containing mesogenic radials in the 2,7-position (JP 05,262,744).

Since the development, of ferroelectric liquid-crystal mixtures in particular, can in no way be regarded as complete, the manufacturers of displays are interested in a very wide variety of components for mixtures. Another reason for this is that only the interaction of the liquid-crystalline mixtures with the individual components of the display device or of the cells (for example the alignment layer) allows conclusions to be drawn on the quality of the liquid-crystalline mixtures too.

OBJECT OF THE INVENTION

The object of the present invention was therefore to provide novel compounds which are suitable in liquid-crystalline mixtures for improving the property profile of these mixtures.

It has now been found, surprisingly, that certain 3,8-disubstituted phenanthridine derivatives are particularly suitable for use in ferroelectric liquid-crystal mixtures.

SUMMARY OF THE INVENTION

The invention relates to a ferroelectric liquid-crystal mixture containing one or more phenanthridine derivatives of the formula (I)

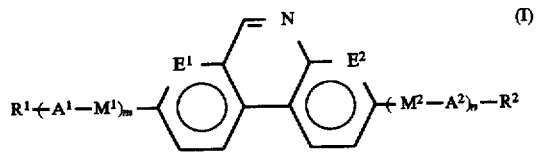

in which the symbols and indices have the following meanings:

$E^1$ and $E^2$ are identical or different and are —N—, —CF— or —CH—;

$R^1$ and $R^2$ are identical or different and are a straight-chain or branched alkyl radical having 1 to 20 carbon atoms (with or without an asymmetrical carbon atom), where one or more —$CH_2$— groups may also be replaced by —O—, —S—, —C≡C—, cyclopropane-1,2-diyl or —Si($CH_3$)$_2$— with the proviso that oxygen and sulfur atoms must not be bonded directly to one another, and where one or more hydrogen atoms of the alkyl radical may also be replaced by fluorine or are one of the following chiral groups (optically active or racemic):

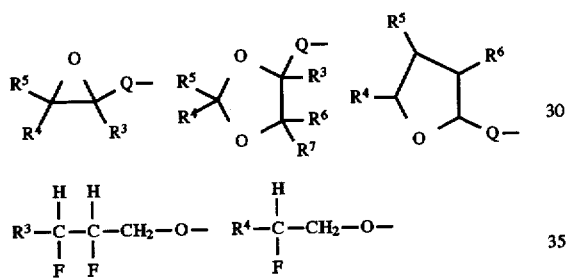

or one of the two groups $R^1$ and $R^2$ can alternatively be hydrogen;

$R^3$, $R^4$, $R^5$, $R^6$ and $R^7$ are identical or different and are hydrogen or a straight-chain or branched alkyl radical having 1 to 16 carbon atoms (with or without an asymmetrical carbon atom), where one —$CH_2$— group may also be replaced by —O— and where one or more hydrogen atoms of the alkyl radical may be replaced by fluorine; $R^4$ and $R^5$ may also together be —($CH_2$)$_4$— or —($CH_2$)$_5$— if they are bonded to a dioxolane system;

Q is —$CH_2$—O—, —CO—O— or a single bond;

$M^1$ and $M^2$ are identical or different and are —CO—O—, —O—CO—, —$CH_2$—O—, —O—$CH_2$—, —$CH_2$—$C_2$—, —C≡C—, or a single bond;

$A^1$ and $A^2$ are identical or different and are 1,4-phenylene, in which one or more H atoms may be replaced by F, trans-1,4-cyclohexylene, pyrimidine-2,5-diyl, pyridine-2,5-diyl, where one H atom may be replaced by F, 1,3,4-thiadiazole-2,5-diyl, 1,3-dioxane-2,5-diyl, 1,3-dithiane-2,5-diyl, 1,3-thiazole-2,4-diyl, 1,3-thiazole-2,5-diyl, thiophene-2,4-diyl or thiophene-2,5-diyl;

m and n are zero or one, but their sum is at most one.

Even addition of very small amounts of phenanthridine derivatives of the formula (I) gives ferroelectric liquid-crystal mixtures having high negative values for the dielectric anisotropy;

DESCRIPTION OF THE PREFERRED EMBODIMENTS

The ferroelectric liquid-crystal mixture preferably contains one or more compounds of the formula (I) in which the group:

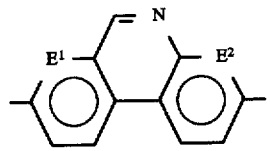

has one of the following meanings:

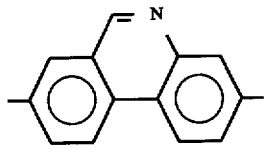

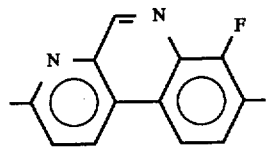

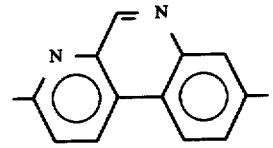

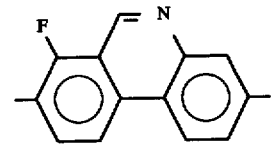

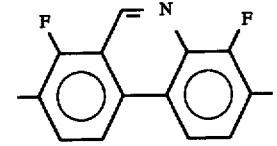

Of these, particular preference is given to compounds of the formula (I) in which $R^1$ and $R^2$ are straight-chain or branched alkyl radicals (with or without an asymmetrical carbon atom) having 1 to 16 carbon atoms, where one or more $CH_2$ groups may also be replaced by —O—, cyclopropane-1,2-diyl or —Si($CH_3$)$_2$—, with the proviso that oxygen atoms must not be bonded directly to one another, and/or in which one or more H atoms of the alkyl radicals may also be replaced by F.

Particular preference is furthermore given, for use in ferroelectric liquid-crystal mixtures, to the following groups of compounds of the formula (I) in which $R^1$ and $R^2$ are straight-chain or branched alkoxy radicals having 1 to 10 carbon atoms, where a —$CH_2$— group separated from the ring by at least two further —$CH_2$— groups may also be replaced by —Si($CH_3$)$_2$:

a) 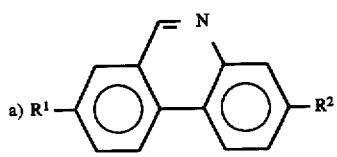

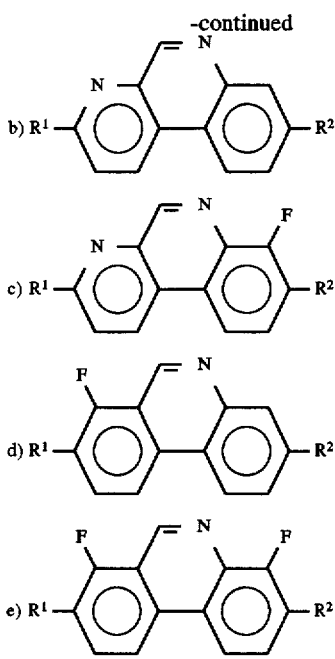

The invention also relates to the use of phenanthridine derivatives of the formula (I) in ferroelectric liquid-crystal mixtures.

Some of the phenanthridine derivatives of the formula (II) are known and some are novel.

The invention therefore furthermore relates to phenanthridine derivatives of the formula (1A)

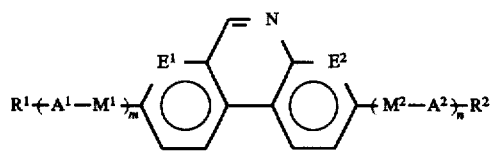

in which the symbols and indices have the following meanings:

$E^1$ and $E^2$ are identical or different and are —N—, —CF— or —CH—;

$R^1$ and $R^2$ are identical or different and are a straight-chain or branched alkyl radical having 1 to 20 carbon atoms (with or without an asymmetrical carbon atom), where one or more —CH$_2$— groups may also be replaced by —O—, —S—, —C≡C—, cyclopropane-1,2-diyl or —Si(CH$_3$)$_2$— with the proviso that oxygen and sulfur atoms must not be bonded directly to one another, and where one or more hydrogen atoms of the alkyl radical may also be replaced by fluorine or are one of the following chiral groups (optically active or racemic):

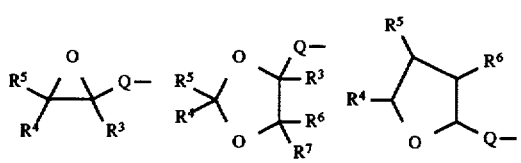

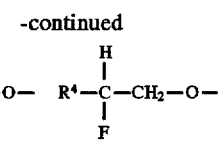

$R^3$, $R^4$, $R^5$, $R^6$ and $R^7$ are identical or different and are hydrogen or a straight-chain or branched alkyl radical having 1 to 16 carbon atoms (with or without an asymmetrical carbon atom), where one —CH$_2$— group may also be replaced by —O— and where one or more hydrogen atoms of the alkyl radical may be replaced by fluorine; $R^4$ and $R^5$ may also together be —(CH$_2$)$_4$— or —(CH$_2$)$_5$— if they are bonded to a dioxolane system;

Q is —CH$_2$—O—, —CO—O— or a single bond;

$M^1$ and $M^2$ are identical or different and are —CO—O—, —O—CO—, —CH$_2$—O—, —O—CH$_2$—, —CH$_2$—CH$_2$—, —C≡C—, or a single bond;

$A^1$ and $A^2$ are identical or different and are 1,4-phenylene, in which one or more H atoms may be replaced by F, trans-1,4-cyclohexylene, pyrimidine-2,5-diyl, pyridine-2,5-diyl, where one H atom may be replaced by F, 1,3,4-thiadiazole-2,5-diyl, 1,3-dioxane-2,5-diyl, 1,3-dithiane-2,5-diyl, 1,3-thiazole-2,4-diyl, 1,3-thiazole-2,5-diyl, thiophene-2,4-diyl or thiophene-2,5-diyl;

m and n are zero or one, but their sum is at most one.

Preferred phenanthridine derivatives of the formula (Ia) conform to those of the formula (I).

The compounds according to the invention are prepared by methods known per se from the literature, as described in standard works on organic synthesis, for example Houben-Weyl, Methoden der Organischen Chemie [Methods of Organic Chemistry], Georg-Thieme-Verlag, Stuttgart.

The preparation is carried out under reaction conditions which are known and suitable for said reactions. Use may also be made here of variants which are known per se, but are not described here in greater detail.

If desired, the starting materials can also be formed in situ, by not isolating them from the reaction mixture, but instead immediately converting them further into the compounds of the formula (I).

For the preparation of phenanthridine derivatives, reference is made to Advanc. Heterocyclic Chem. 13, 315 (1971); Khim. Geterosikl. Soedin 1969, 1044 (C.A. 1970, 72, 111265 w); Tetrahedron 1981, 37, 825; Zh. Org. Khim. 1978, 14, 891 (C.A. 1978, 89, 24118 h); J. Chem. Soc. Perkin Trans. I, 1972, 113; Org. Reactions 1984, 30, 1; Synthesis 1985, 107; Heterocycles 1980, 14, 1567; Acc. Chem. Res. 1978, 11, 283; Tetrahedron 1984, 40, 1919; Tetrahedron Lett. 29, 5463 (1988); Chem. Scripta 1986, 26, 311.

Methods of this type which are known from the literature are described in greater detail below in schemes 1-3 for three preferred groups of compounds of the formulae (I) and (Ia).

Scheme 1:

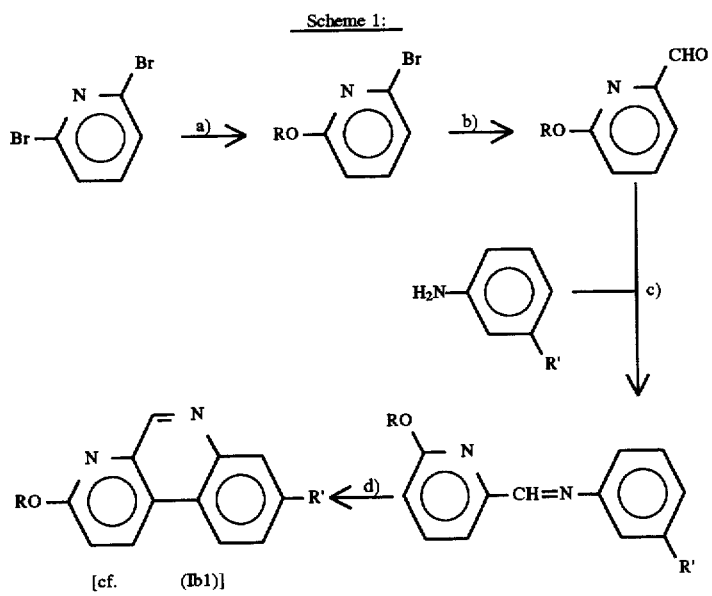

a) NaOR in ROH b) 1. BuLi; 2. DMF; 3. H⁺; analogous to J. Org. Chem. 51, 3762 (1986)

c) for example analogously to Angew. Chemie 81, 903 (1969)

d) h.γ/O₂; for example analogously to J. Am. Chem. Soc. 84, 4361 (1962)

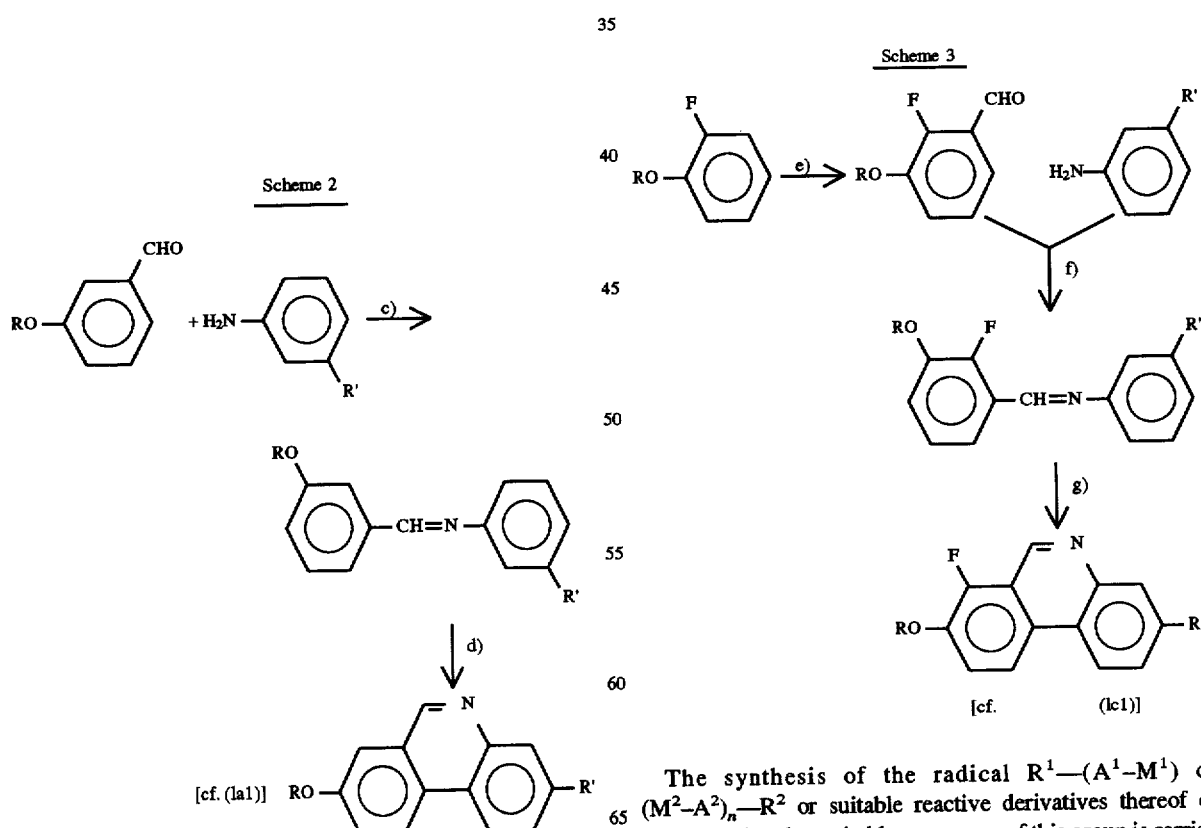

The synthesis of the radical $R^1$—$(A^1$–$M^1)$ or $(M^2$–$A^2)_n$—$R^2$ or suitable reactive derivatives thereof or alternatively other suitable precursors of this group is carried out by methods known to the person skilled in the art.

For the synthesis of specific aromatic rings, a constituent of the compounds of the formulae (I) and (Ia), reference is made to DE-A 23 44 732, 24 50 088, 24 29 093, 25 02 904, 26 36 684, 27 01 591 and 27 52 975 for compounds containing 1,4-cyclohexylene and 1,4-phenylene groups; DE-A 26 41 724 for compounds containing pyrimidine-2,5-diyl groups; DE-A 40 26 223 and EP-A 03 91 203 for compounds containing pyridine-2,5-diyl groups; DE-A 32 31 462 for compounds containing pyridazine-3,6-diyl groups; N. Miyaura, T. Yanagi and A. Suzuki in Synthetic Communications 11 (1981), 513–519, DE-C-39 30 663, M. J. Sharp, W. Cheng, V. Snieckus in Tetrahedron Letters 28 (1987) 5093ff; G. W. Gray in J. Chem. Soc. Perkin Trans II 1989, 2041ff and Mol. Cryst. Liq. Cryst. 172 (1989) 165ff, 204 (1991) 43ff and 91ff; EP-A 0 449 015; WO 89/12039; WO 89/03821; EP-A 0 354 434 for the direct linking of aromatics and heteroaromatics; DE-A 32 01 721 for compounds containing —$CH_2CH_2$— bridges, and Koji Seto et al. in Liquid Crystals 8 (1990) 861–870 for compounds containing —C≡C— bridges.

The preparation of disubstituted pyridines, disubstituted pyrazines, disubstituted pyrimidines and disubstituted pyridazines is also given, for example, in the corresponding volumes in the series "The Chemistry of Heterocyclic Compounds" by A. Weissberger and E. C. Taylor (Editors).

Dioxane derivatives are expediently prepared by reaction of a corresponding aldehyde (or a reactive derivative thereof) with a corresponding 1,3-diol (or a reactive derivative thereof), preferably in the presence of an inert solvent, such as benzene or toluene, and/or in the presence of a catalyst, for example a strong acid, such as sulfuric acid, benzenesulfonic acid or p-toluenesulfonic acid, at temperatures between about 20° C. and about 150° C., preferably between 80° C. and 120° C. Primarily suitable reactive derivatives of the starting materials are acetals.

Some of said aldehydes and 1,3-diols and reactive derivatives thereof are known and some can be prepared without difficulty by standard methods of organic chemistry from compounds known from the literature. For example, the aldehydes are obtainable by oxidation of corresponding alcohols or by reduction of nitriles or corresponding carboxylic acids or derivatives thereof, and the diols are obtainable by reduction of corresponding diesters.

Compounds in which an aromatic ring is substituted by at least one F atom can also be obtained from the corresponding diazonium salts by replacement of the diazonium group by a fluorine atom, for example by the methods of Balz and Schiemann.

As far as the linking of ring systems to one another is concerned, reference may be made, for example, to: N. Miyaura, T. Yanagai and A. Suzuki in Synthetic Communications 11 (1981), 513–519, DE-C-39 30 663, M. J. Sharp, W. Cheng, V. Snieckus in Tetrahedron Letters 28 (1987) 5093; G. W. Gray in J. Chem. Soc. Perkin Trans II 1989, 2041 and Mol. Cryst. Liq. Cryst. 172 (1989) 165, 204 (1991) 43 and 91; EP-A 0 449 015; WO-A 89/12039; WO-A 89/03821; EP-A 0 354 434 for the direct linking of aromatics and heteroaromatics; DE-A 32 01 721 for compounds containing —$CH_2CH_2$— bridges, and Koji Seto et al. in Liquid Crystals 8 (1990) 861–870 for compounds containing —C≡C— bridges.

Esters of the formula (I) can also be obtained by esterification of corresponding carboxylic acids (or reactive derivatives thereof) using alcohols or phenols (or reactive derivatives thereof) or by the DCCI method (DCCI= dicyclohexylcarbodiimide).

The corresponding carboxylic acids and alcohols or phenols are known and can be prepared analogously to known processes.

Particularly suitable reactive derivatives of said carboxylic acids are the acid halides, especially the chlorides and bromides, furthermore the anhydrides, for example also mixed anhydrides, azides or esters, in particular alkyl esters having 1–4 carbon atoms in the alkyl group.

Particularly suitable reactive derivatives of said alcohols and phenols are the corresponding metal alkoxides or phenoxides, preferably of an alkali metal, such as sodium or potassium.

The esterification is advantageously carried out in the presence of an inert solvent. Particularly suitable solvents are ethers, such as diethyl ether, di-n-butyl ether, THF, dioxane or anisole, ketones, such as acetone, butanone or cyclohexanone, amides, such as DMF or hexamethylphosphoric triamide, hydrocarbons, such as benzene, toluene or xylene, halogenated hydrocarbons, such as tetrachloromethane, dichloromethane or tetrachloroethylene, and sulfoxides, such as dimethyl sulfoxide or sulfolane.

Ethers of the formula (I) are obtainable by etherification of corresponding hydroxyl compounds, preferably corresponding phenols, where the hydroxyl compound is expediently first converted into a corresponding metal derivative, for example into the corresponding alkali metal alkoxide or alkali metal phenoxide by treatment with NaH, $NaNH_2$, NaOH, KOH, $Na_2CO_3$ or $K_2CO_3$. This can then be reacted with the corresponding alkyl halide, alkyl sulfonate or dialkyl sulfate, expediently in an inert solvent, such as acetone, 1,2-dimethoxyethane, DMF or dimethylsulfoxide, or alternatively with an excess of aqueous or aqueous/alcoholic NaOH or KOH at temperatures between about 20° and 100° C.

Regarding the synthesis of specific radicals R, reference may additionally be made, for example, to EP-A 0 355 008 for compounds with silicon-containing side chains and to EP-A 0 292 954 and EP-A 0 398 155 for compounds containing cyclopropyl groups in the side chain.

The provision of ferroelectric liquid-crystal mixtures containing compounds of the formula (I) very generally considerably broadens the range of liquid-crystalline mixtures which are suitable, from various application points of view.

In this connection, the compounds of the formula (I) have a broad range of applications. Depending on the choice of substituents, they can be used as base materials from which liquid-crystalline phases according to the invention are predominantly composed; however, compounds of the formula (I) can also be added to liquid-crystalline base materials from other classes of compound, in order, for example, to modify the dielectric and/or optical anisotropy of a novel dielectric and/or to optimize its threshold voltage and/or its viscosity. The compounds of the formula (I) are particularly suitable, even when admixed in small amounts, for modifying the dielectric anisotropy, $\Delta\epsilon$, toward higher negative values.

The liquid-crystal mixtures according to the invention generally contain from 2 to 35, preferably from 2 to 25, particularly preferably from 2 to 20 components.

They generally contain from 0.01 to 80% by weight, preferably from 0.1 to 60% by weight, particularly preferably from 0.1 to 30% by weight, of one or more, preferably 1 to 10, particularly preferably 1 to 5, very particularly preferably 1 to 3, of the compounds of the formula (I) according to the invention.

Further components of liquid-crystal mixtures according to the invention are preferably selected from known compounds having smectic and/or nematic and/or cholesteric and/or antiferroelectric phases. These include, for example:

derivatives of phenylpyrimidine, as described, for example, in WO 86/06401 and U.S. Pat. No. 4,874,542, meta-substituted aromatic compounds having a six-membered ring, as described, for example, in EP-A 0 578 054, silicon compounds, as described, for example, in EP-A 0 355 008, mesogenic compounds containing only one side chain, as described in EP-A 0 541 081, hydroquinone derivatives, as described, for example, in EP-A 0 603 786, pyridylpyrimidines, as described, for example, in WO 92/12974, phenylbenzoates, as described, for example, in P. Keller, Ferroelectrics 58 (1984), 3, and J. W. Goodby et al., Liquid Crystals and Ordered Fluids, Vol. 4, New York, 1984, and thiadiazoles as described, for example, in EP-A 0 309 514.

Examples of suitable chiral, non-racemic dopes are:

optically active phenylbenzoates, as described, for example, in P. Keller, Ferroelectrics 58 (1984), 3, and J. W. Goodby et al., Liquid Crystals and Ordered Fluids, Vol. 4, New York, 1984, optically active oxirane ethers, as described, for example, in EP-A 0 263 437 and WO-A 93/13093, optically active oxirane esters, as described, for example, in EP-A 0 292 954, optically active dioxolane ethers, as described, for example, in EP-A 0 351 746, optically active dioxolane esters, as described, for example, in EP-A 0 361 272, and optically active tetrahydrofuran-2-carboxylic esters, as described, for example, in EP-A 0 355 561.

The novel mixtures can in turn be used in electro-optical or fully optical elements, for example display elements, switching elements, light modulators, elements for image processing and/or signal processing or generally in the area of nonlinear optics.

Novel liquid-crystalline mixtures containing compounds of the formula (I) are particularly suitable for use in electro-optical switching and display devices (displays). These displays are usually constructed in such a way that a liquid-crystal layer is enclosed on both sides by layers, which are usually, in this sequence starting from the LC layer, at least one alignment layer, electrodes and a limiting sheet (for example of glass). In addition, they contain spacers, adhesive frames, polarizers and, for color displays, thin color-filter layers. Other possible components are antireflection, passivation, compensation and barrier layers and electric non-linear elements, such as thin-film transistors (TFTs) and metal-insulator-metal (MIM) elements. The structure of liquid-crystal displays has already been described in detail in relevant monographs (see, for example, E. Kaneko, "Liquid Crystal TV Displays: Principles and Applications of Liquid Crystal Displays", KTK Scientific Publishers 1987).

The mixtures are furthermore suitable for field treatment, i.e. for operation in the quasi-bookshelf geometry (QBG) (see, for example, H. Rieger et al., SID 91 Digest (Anaheim), 1991, p. 396).

The novel mixtures are likewise suitable for use in ferroelectric liquid-crystal displays which are based on utilization of the DHF effect or the PSFLCD effect (pitch stabilized ferroelectric liquid-crystal display, also known as SBF, short pitch bistable ferroelectric effect).

The present invention is described in greater detail by means of the following examples, but this is not intended to represent a limitation.

EXAMPLE 1:

4-Fluoro-8-methoxy-3-octyloxyphenanthridine

A solution of 2.5 g of 2-fluoro-3-octyloxybenzaldehyde (prepared by reacting 2-octyloxyfluorobenzene with lithium diisopropylamide followed by reaction with N,N-dimethylformamide) in 50 ml of toluene is heated at 110° C. for 30 minutes with 1.4 g of 3-methoxyaniline. Removal of the solvent by vacuum distillation in a rotary evaporator gives crude (2-fluoro-3-octyloxy)benzylidene(3-methoxy) aniline. This is dissolved in cyclohexane with addition of 4 mol % of iodine and exposed to UV light for 8 hours at 25° C. in a quartz apparatus. Chromatography on $SiO_2$ using dichloromethane and recrystallization from acetonitrile gives 0.8 g of 4-fluoro-8-methoxy-3-octyloxyphenanthridine.

The following are obtained analogously to Example 1:
Ex. 2 8-Decyloxy-4-fluoro-3-octyloxyphenanthridine
Ex. 3 4,7-Difluoro-3,8-bis(octyloxy)phenanthridine
Ex. 4 7-Fluoro-3,8-bis(hexyloxy)phenanthridine
Ex. 5 8-Methoxy-3-octyloxy-4-azaphenanthridine
Ex. 6 8-Heptyloxy-3-octyloxy-4-azaphenanthridine
Ex. 7 7-Fluoro-3,8-bis(octyloxy)-4-azaphenanthridine
Ex. 8 7-Fluoro-3-(4-butyldimethylsilyl)butyloxy-8-octyloxyphenanthridine
Ex. 9 4-Fluoro-3-octyloxyphenanthridine
Use Example 1

A ferroelectric liquid-crystal mixture comprising

| | Proportions by weight |
|---|---|
| 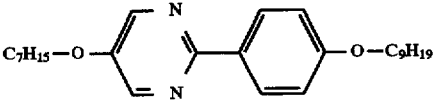 | 3.77% |
| 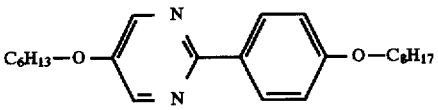 | 4.25% |

| | Proportions by weight |
|---|---|
| 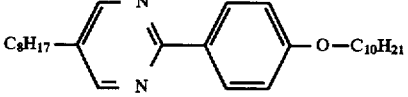 | 4.70% |
| 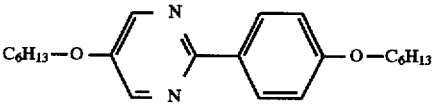 | 3.95% |
| 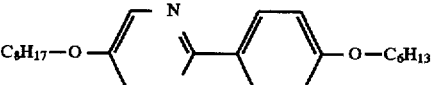 | 4.25% |
| 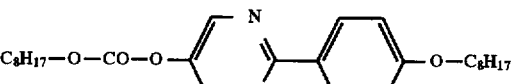 | 8.00% |
| 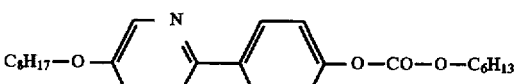 | 7.47% |
| 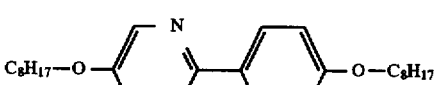 | 4.56% |
| 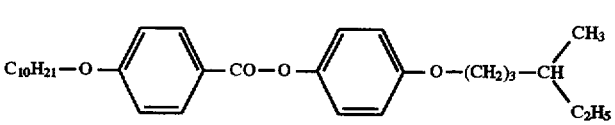 | 8.11% |
| 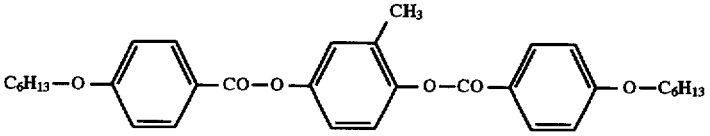 | 2.30% |
| 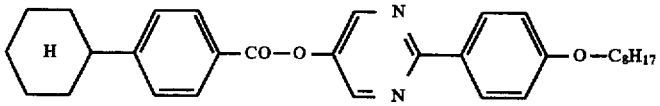 | 3.22% |
| 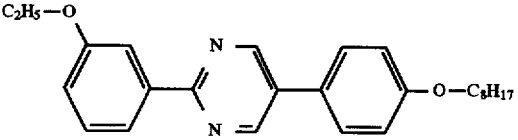 | 6.36% |
| 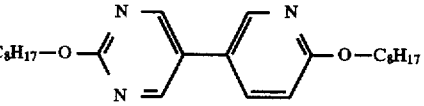 | 3.61% |
| 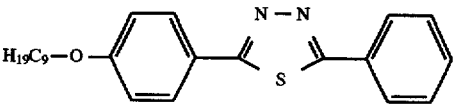 | 5.92% |

-continued

| | Proportions by weight |
|---|---|
| C₈H₁₇—O—〔phenyl〕—CH=N—〔pyridine with F〕—〔phenyl〕—O—C₄H₈—Si(CH₃)₂—C₄H₉ | 7.32% |
| C₈H₁₇—O—〔phenyl〕—〔phenyl〕—O—CO—〔phenyl〕—O—C₄H₈—Si(CH₃)₂—C₄H₉ | 8.06% |
| C₄H₉—C(=S)(S)—CH₂—O—〔pyrimidine〕—〔phenyl〕—O—CH₂—C(=S)(S)—C₄H₉ trans | 2.73% |
| C₆H₁₃—O—〔phenyl〕—〔pyrimidine〕—〔phenyl〕—O—CO—C(R)(R)—C₃H₇ | 6.71% |
| C₈H₁₇—O—〔pyrimidine〕—〔phenyl〕—O—CH₂—〔spiro dioxolane cyclohexane〕 (S) | 2.00% |
| [crown ether with N—CO—C(CH₃)₃ substituent] | 0.65% |
| H₁₃C₆O—〔phenanthridine〕—OC₆H₁₃ | 2.14% | has the following liquid-crystalline phase ranges:

X –29 S$_C$* 74 S$_A$ 86 N* 95 I

The spontaneous polarization at 25° C. is 40 n C/cm².

Use Example 2

A ferroelectric liquid-crystalline mixture comprising
4.6% by wt. of 2-(4-ethoxyphenyl)-5-octyloxypyrimidine
12.6% by wt. of 2-(4-butoxyphenyl)-5-octyloxypyrimidine
13.9% by wt. of 2-(4-hexyloxyphenyl)-5-octyloxypyrimidine
6.4% by wt. of 9-octyloxy-2-(4-octyloxyphenyl)-pyrimidine
26.9% by wt. of 2-[4-(10-undecen-1-yl)oxyphenyl]-5-octylpyrimidine
11.4% by wt. of 4-(5-octyloxypyrimidin-2-yl)phenyl trans-4-pentylcyclohexanecarboxylate
10.7% by wt. of 4-[2-((S)-7-methylmonyloxy)pyrimidin-5-yl]phenyl (2S, 3S)-2-chloro-3-methylpentanoate
1.0% by wt. of 5-[4-((S)-3,7-dimethyl-oct-6-en-1-yl)oxyphenyl]-2-octyloxypyrimidine is mixed with 1.95% by wt. of 4-fluoro-6-hexyloxy-3-octyloxyphenanthridine; the X/S$_C$* transition rises from –1° to 0° C., the S$_C$*/S$_A$ transition falls from 71° to 69° C., the S$_A$/N* transition remains unchanged at 79° C., while Δε (20 KH₂) changes from –0.8 to –1.0.

This example shows that the dielectric anisotropy can be customized using only small amounts of the novel compounds with good mesophen compatibility.

We claim:

1. A ferroelectric liquid-crystal mixture containing one or more phenanthridine derivatives of the formula (I)

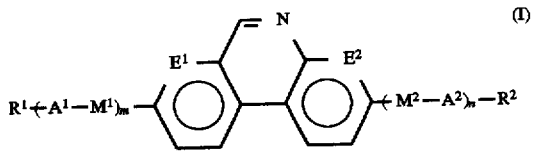

in which the symbols and indices have the following meanings:

$E^1$ and $E^2$ are identical or different and are —CF— or —CH—;

$R^1$ and $R^2$ are identical or different and are a straight-chain or branched alkyl radical having 1 to 20 carbon atoms (with or without an asymmetrical carbon atom), where one or more —CH$_2$— groups may also be replaced by —O—, cyclopropane-1,2-diyl or —Si(CH$_3$)$_2$— with the proviso that oxygen atoms must not be bonded directly to one another, and where one or more hydrogen atoms of the alkyl radical may also be replaced by fluorine; and m and n are zero.

2. A ferroelectric liquid-crystal mixture as claimed in claim 1, which contains a compound of the formula (I) in which the group

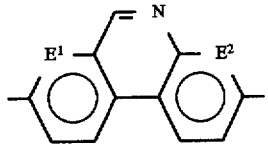

has one of the following meanings:

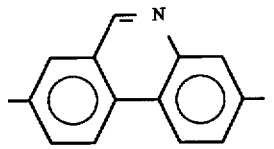

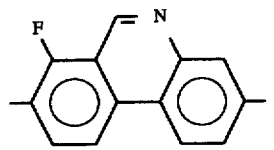

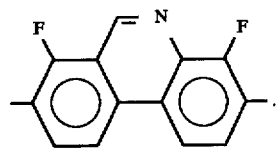

3. A ferroelectric liquid-crystal mixture as claimed in claim 1, which contains a compound of the formula (I) from the following group, where $R^1$ and $R^2$ are straight-chain or branched alkoxy radicals having 1 to 10 carbon atoms, where a —CH$_2$— group which is separated from the ring by at least two further —CH$_2$— groups may also be replaced by —Si(CH$_3$)$_2$:

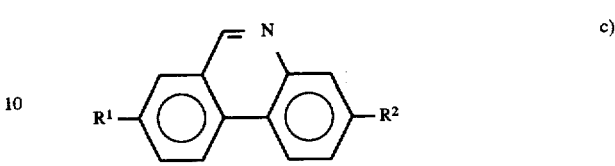

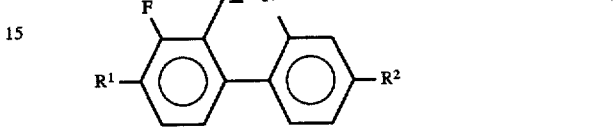

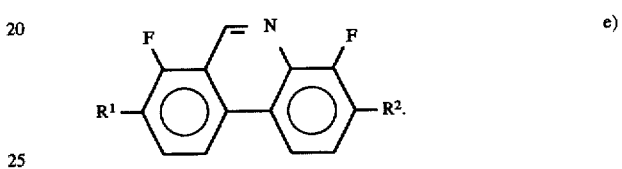

4. A ferroelectric liquid-crystal mixture as claimed in claim 1, which comprises 2 to 20 components and contains 1 to 10 compounds of the formula (I).

5. A ferroelectric liquid-crystal mixture as claimed in claim 1, which contains from 0.01 to 80% by weight of one or more compounds of the formula (I).

6. An electro-optical switching and/or display element which contains a ferroelectric liquid-crystal mixture as claimed in claim 1.

* * * * *